United States Patent [19]

Brown

[11] 4,031,121
[45] June 21, 1977

[54] ORGANOBROMOSILICONE FLUIDS

[75] Inventor: Paul L. Brown, Saginaw, Mich.

[73] Assignee: Dow Corning Corporation, Midland, Mich.

[22] Filed: Sept. 22, 1976

[21] Appl. No.: 725,318

[52] U.S. Cl. .......................... 260/448.8 R; 252/8.6; 106/15 FP
[51] Int. Cl.² ............................................ C07F 7/18
[58] Field of Search ............................. 260/448.8 R

[56] References Cited

UNITED STATES PATENTS

| 3,299,173 | 1/1967 | Roselli | 260/448.8 R X |
| 3,334,123 | 8/1967 | Culpepper | 260/448.8 R |

Primary Examiner—Paul F. Shaver
Attorney, Agent, or Firm—Jack E. Moermond

[57] ABSTRACT

Organobromosilicone fluids having the general formula $(BrCH_2)_3CCH_2O(R_2SiO)_xCH_2C(CH_2Br)_3$ wherein each R is selected from the group consisting of hydrocarbon radicals containing from 1 to 18 carbon atoms, fluorinated hydrocarbon radicals containing from 1 to 18 carbon atoms, chlorinated hydrocarbon radicals containing from 1 to 18 carbon atoms and cyanohydrocarbon radicals containing from 1 to 18 carbon atoms, and $x$ has a value of from 1 to 20 are disclosed. These fluids are useful, for example, for improving the fire resistance of cellulosic substrates.

8 Claims, No Drawings

ORGANOBROMOSILICONE FLUIDS

The use of halogenated compounds of various kinds in flame-retardant applications is well documented in the literature. This is particularly true of the halogenated organic compounds.

The newly discovered organobromosilicone fluids of this invention also find utility in flame-retardant applications. Thus, the number of materials available to those working in the flame-retardant field has been significantly increased and makes it more feasible for them to match up the best materials for particular applications. Moreover, it is conceivable that the unique combination of the organobromo moiety and the silicone moiety in the fluids of this invention will result in unusual properties in particular end uses.

more specifically, this invention relates to a silicone fluid having the general formula $$(BrCH_2)_3CCH_2O(R_2SiO)_xCH_2C(CH_2Br)_3$$

wherein each R is independently selected from the group consisting of hydrocarbon radicals containing from 1 to 18 carbon atoms, fluorinated hydrocarbon radicals containing from 1 to 18 carbon atoms, chlorinated hydrocarbon radicals containing from 1 to 18 carbon atoms and cyanohydrocarbon radicals containing from 1 to 18 carbon atoms, and x has a value of from 1 to 20.

Illustrative examples of the R radicals in the above formula include the methyl, ethyl, propyl, isopropyl, butyl, tertiary butyl, amyl, hexyl, octyl, 2-ethylhexyl, decyl, dodecyl, octadecyl, vinyl, allyl, hexenyl, dodecenyl, propargyl, cyclohexyl, phenyl, benzyl, tolyl, biphenylyl, naphthyl, 3,3,3-trifluoropropyl, 3,3,4,4,5,5,5-heptafluoropentyl, alpha,alpha,alpha-trifluorotolyl, perfluorocyclohexyl, 3-chloropropyl, 4-chlorobutyl, 2-cyanoethyl, 3-cyanopropyl, and 1,3-dicyanophenyl radicals. Of these radicals, the methyl and phenyl radicals are preferred at this time.

As noted above, there can be from 1 to 20 of the silicone units in the fluids of this invention. It is believed, however, that when the average value of x begins to substantially exceed 10 the beneficial flame-retardant properties of the fluids of this invention falls off rapidly.

The organobromosilicone fluids of this invention can be prepared by reacting tribromoneopentyl alcohol with an acetoxy endblocked silicone fluid in the presence of a suitable catalyst. This method will be illustrated in more detail in the examples below. In light of this information other methods by which the fluids of this invention can be prepared will be apparent to those skilled in the art.

The organobromosilicone fluids of this invention can be applied to cellulosic substrates to improve their fire resistance by any of the well known means such as by spraying, dipping, padding, nip roll and the like. The amount of the organobromosilicone fluid applied to the substrate will vary depending on the particular substrate and the effect desired. Generally speaking, however, the amount of add-on of the organobromosilicone fluid will be in the range of 0.1 to 5.0 percent by weight.

As noted above, the organobromosilicone fluids of this invention can be applied to various substrates, particularly cellulosic substrates to improve their flame retardant properties. Examples of such substrates include wood, jute, cotton, or hemp in the form of plywood panels, rope or textiles, for example, as well as to substrates made of nylon, polyamides, rayon or the like.

Now in order that those skilled in the art may better understand how the present invention can be practiced, the following examples are given by way of illustration and not by way of limitation. All parts and percents referred to herein are by weight and all viscosities are measured at 25° C. unless otherwise specified.

EXAMPLE 1

To a three-necked flask equipped with stirrer, condenser, dropping funnel, ammonia sparger and heating mantle there was added 162.3 g. of $(BrCH_2)_3CCH_2OH$ and 200 ml. of toluene. The mixture was saturated with ammonia and then 81 g. of $CH_3COO[(CH_3)_2SiO]_3OCCH_3$ was slowly added while heating the mixture at 90° C. The heating completes the reaction more quickly. The salt (ammonium acetate) was washed from the mixture using two water washings. Then the toluene and most of the low boiling components were removed by stripping over a short, open column at a head temperature of about 130° C. and a pot temperature of about 240° C. at 0.25 mm. of mercury pressure using a nitrogen sweep. The resulting product, $$(BrCH_2)_3CCH_2O[(CH_3)_2SiO]_3CH_2C(CH_2Br)_3,$$

was dark in color with a viscosity of 73.6 cs. and a refractive index at 25° C. of 1.5071. The product had a purity of greater than 95 percent by gas-liquid chromatography analysis.

The infrared analysis spectrum shows the presence of $Si(CH_3)_2$ at 2806 and 1260 cm$^{-1}$, OCH at about 1414 and 1427 cm$^{-1}$, and SiOSi and SiOC at 1020 to 1130 cm$^{-1}$. The SiOSi and SiOC region suggests that the degree of polymerization is greater than 3, but the hydrogen nuclear magnetic resonance analysis shows that the proton ratios are correct for the trimer structure.

EXAMPLE 2

The procedure of Example 1 was repeated except that the reactants were 124 g. of $(BrCH_2)_3CCH_2OH$, 250 g. of $CH_3COO[(CH_3)_2SiO]_{~15.4}OCCH_3$ and 350 ml. of toluene, and stripping was to a 200° C. pot temperature at 1 mm. of mercury pressure. The product, $(BrCH_2)_3CCH_2O[(CH_3)_2SiO]_{~15.4}CH_2C(CH_2Br)_3$, had a viscosity of 43.5 cs. and a refractive index at 25° C. of 1.4392.

EXAMPLE 3

The products of Examples 1 and 2 were tested for flame-resistant characteristics using the following tests.

Manifold Test

This test is the one described in Federal Test Methods No. 791A, Method 6053 "Manifold Ignition Test." In this test the test fluid is preheated to 450°±5° F. and then dropped at the rate of 100 drops per minute from a dropping funnel whose outlet is five inches above the center of the manifold. The surface temperature of the manifold is varied from 600° to 1200° F. in 100° increments. The minimum temperature at which the fluid burns is recorded.

Kim-Wipe Test

In this test a Kim-Wipe tissue is soaked with the test fluid. A bunsen burner is then held to the tissue for 5 seconds followed by cooling for 5 seconds, a total of four consecutive heating and cooling cycles being used.

Aluminum Dish Test

About seven grams of the test fluid is placed in a small aluminum dish or cup in this test. The fluid is heated continuously with a bunsen burner to see if it will ignite or burn.

The results of these tests are set forth in the following table.

| Test Fluid | Manifold | Kim-Wipe | Aluminum Dish |
|---|---|---|---|
| Example 1 | ~1040° F. | No ignition | No ignition after flame from burner removed. |
| Example 2 | ~1020° F. | Burns slowly | Burns with low flame after burner removed. |

EXAMPLE 4

When the siloxanes set forth below are substituted for the siloxane reactant of Example 1 in equivalent amounts, the indicated products are obtained.

| SILOXANE | PRODUCT |
|---|---|
| $CH_3COO[(CH_3)C_6H_5SiO]_5OCCH_3$ | $(BrCH_2)_3CCH_2O[(CH_3)C_6H_5SiO]_5CH_2C(CH_2Br)_3$ |
| $CH_3COO[(CH_3)_2SiO]_3[(CH_3)C_6H_5SiO]_{10}OCCH_3$ | $(BrCH_2)_3CCH_2O[(CH_3)_2SiO]_3[(CH_3)C_6H_5SiO]_{10}CH_2C(CH_2Br)_3$ |
| $CH_3COO[(CH_3)CF_3CH_2CH_2SiO]_3OCCH_3$ | $(BrCH_2)_3CCH_2O[(CH_3)CF_3CH_2CH_2SiO]_3CH_2C(CH_2Br)_3$ |
| $CH_3COO[(CH_3)ClCH_2CH_2CH_2SiO]_{20}OCCH_3$ | $(BrCH_2)_3CCH_2O[(CH_3)ClCH_2CH_2CH_2SiO]_{20}CH_2C(CH_2Br)$ |
| $CH_3COO[(CH_3)NCCH_2CH_2SiO]_{10}OCCH_3$ | $(BrCH_2)_3CCH_2O[(CH_3)NCCH_2CH_2SiO]_{10}CH_2C(CH_2Br)_3$ |
| $CH_3COO[(CH_3)_2SiO]_1OCCH_3$ | $(BrCH_2)_3CCH_2O[(CH_3)_2SiO]_1CH_2C(CH_2Br)_3$ |
| $CH_3COO[(CH_3)C_6H_5SiO]_1OCCH_3$ | $(BrCH_2)_3CCH_2O[(CH_3)C_6H_5SiO]_1CH_2C(CH_2Br)_3$ |

That which is claimed is:

1. A silicone fluid having a general formula $$(BrCH_2)_3CCH_2O(R_2SiO)_xCH_2C(CH_2Br)_3$$

wherein each R is selected from the group consisting of hydrocarbon radicals containing from 1 to 18 carbon atoms, fluorinated hydrocarbon radicals containing from 1 to 18 carbon atoms, chlorinated hydrocarbon radicals containing from 1 to 18 carbon atoms and cyanohydrocarbon radicals containing from 1 to 18 carbon atoms, and x has a value of from 1 to 20.

2. A silicone fluid as defined in claim 1 wherein x has a value of from 1 to 10.

3. A silicone fluid as defined in claim 2 wherein R is a hydrocarbon radical.

4. A silicone fluid as defined in claim 3 wherein R is selected from the group consisting of methyl and phenyl radicals.

5. A silicone fluid as defined in claim 4 wherein some R's are methyl radicals and some R's are phenyl radicals.

6. A silicone fluid as defined in claim 4 wherein all the R's are methyl radicals.

7. A silicone fluid as defined in claim 6 wherein the fluid has the general formula $$(BrCH_2)_3CCH_2O[(CH_3)_2SiO]_3CH_2C(CH_2Br)_3.$$

8. A silicone fluid as defined in claim 6 wherein the fluid has the general formula $$(BrCH_2)_3CCH_2O[(CH_3)_2SiO]_{\sim 15}CH_2C(CH_2Br)_3.$$

* * * * *

UNITED STATES PATENT AND TRADEMARK OFFICE
CERTIFICATE OF CORRECTION

PATENT NO. : 4,031,121
DATED : June 21, 1977
INVENTOR(S) : Paul L. Brown

It is certified that error appears in the above-identified patent and that said Letters Patent are hereby corrected as shown below:

Column 3, line 1, the title "Kim-Wipe Test" should read --Kim-Wipe® Test--.

Column 3, line 2, "Kim-Wipe" should read --Kim-Wipe®--.

Column 3, first table, "Kim-Wipe" should read --Kim-Wipe®--.

Signed and Sealed this

Twenty-second Day of January 1980

[SEAL]

Attest:

SIDNEY A. DIAMOND

Attesting Officer

Commissioner of Patents and Trademarks